(12) United States Patent
Varel et al.

(10) Patent No.: US 9,307,905 B2
(45) Date of Patent: Apr. 12, 2016

(54) INTRAOCULAR PRESSURE SENSING DEVICES AND ASSOCIATED SYSTEMS AND METHODS

(71) Applicant: University of Washington through its Center for Commercialization, Seattle, WA (US)

(72) Inventors: Cagdas Varel, Seattle, WA (US); Tueng T. Shen, Redmond, WA (US); Karl F. Bohringer, Seattle, WA (US); Brian Otis, Seattle, WA (US); Buddy D. Ratner, Seattle, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 14/028,303

(22) Filed: Sep. 16, 2013

(65) Prior Publication Data

US 2015/0045643 A1   Feb. 12, 2015

Related U.S. Application Data

(60) Provisional application No. 61/701,511, filed on Sep. 14, 2012.

(51) Int. Cl.
*A61B 3/16*   (2006.01)
*A61B 5/00*   (2006.01)
*A61B 5/053*   (2006.01)

(52) U.S. Cl.
CPC ............ *A61B 3/16* (2013.01); *A61B 5/0004* (2013.01); *A61B 5/0538* (2013.01); *A61B 5/686* (2013.01); *A61B 5/6821* (2013.01); *Y10T 29/49155* (2015.01)

(58) Field of Classification Search
CPC ........................................................ A61B 3/16
USPC ................................................. 600/398, 345
See application file for complete search history.

(56) References Cited

U.S. PATENT DOCUMENTS

| 4,305,399 A | 12/1981 | Beale et al. |
| 6,579,235 B1 | 6/2003 | Abita et al. |
| 7,481,771 B2 | 1/2009 | Fonseca et al. |

(Continued)

FOREIGN PATENT DOCUMENTS

| WO | 03073959 | 9/2003 |
| WO | 2012137067 A2 | 10/2012 |

OTHER PUBLICATIONS

R. Receveur, F. Lindemans, and N. de Rooij, "Microsystem technologies for implantable applications," *J. Micromechan. Microeng.*, vol. 17, No. 5, p. 50, 2007.

(Continued)

*Primary Examiner* — Brian Szmal
(74) *Attorney, Agent, or Firm* — Perkins Coie LLP

(57) ABSTRACT

The present technology relates generally to intraocular pressure ("IOP") monitoring systems and associated devices and methods. In some embodiments, an intraocular pressure monitoring system configured in accordance with the technology comprises an implantable intraocular assembly and an external unit configured to transmit power to and receive data from the intraocular assembly. The intraocular assembly can include an IOP sensing device embedded within a flexible, expandable annular member. The IOP sensing device can include an antenna, a pressure sensor, and a microelectronic device encapsulated by an elastomer.

18 Claims, 20 Drawing Sheets

(56) References Cited

U.S. PATENT DOCUMENTS

| | | | |
|---|---|---|---|
| 7,909,770 | B2 | 3/2011 | Stern et al. |
| 8,025,625 | B2 | 9/2011 | Allen et al. |
| 8,486,833 | B2 | 7/2013 | Bruzewicz et al. |
| 2012/0238857 | A1* | 9/2012 | Wong et al. .................. 600/398 |
| 2012/0245444 | A1* | 9/2012 | Otis et al. .................... 600/345 |
| 2013/0243655 | A1 | 9/2013 | Li et al. |

OTHER PUBLICATIONS

H. Quigley and A. Broman, "The number of people with glaucoma worldwide in 2010 and 2020," *Brit. J. Ophthalmol.*, vol. 90, No. 3, pp. 262-267, Mat. 2006.

J. H. Liu, X. Zhang, D. F. Kripke, and R. N. Weinreb, "Twenty-four-Hour intraocular pressure pattern associated with early glaucomatous changes," *Investigat. Ophthalmol. Jlis. Sci.*, vol. 44, No. 4, p. 1586. 2003.

S. Asrani, R. Zeimer, J. Wilensky, D. Gieser, S. Vitale, and K. Lindenmuth, "Large diurnal fluctuations in intraocular pressure are an independent risk factor in patients with glaucoma," *J. Glaucoma*, vol. 9, No. 2, pp. 134-142, Apr. 2000.

T. Kakaday, A. W. Hewitt, N. H. Voelcker, J. S. J. Li, and J. E. Craig, "Advances in telemetric continuous intraocular pressure assessment," *Brit. J. Ophthalmol.*, vol. 93, No. 8, pp. 992-996, 2009.

Y.-C. Shih, T. T. Shen, and B. P. Otis, "A 2.3 µW wireless intraocular pressure/temperature monitor," in *Proc. IEEE Asian Solid.State Circuits Conf.* (A-SSCC 2010). 2010, pp. 237-240.

K. Stangel, S. Kolnsberg, D. Hammerschmidt, B. Hosticka, H. Trieu, and W. Mokwa, "A programmable intraocular CMOS pressure sensor system implant," *IEEE J. Solid-State Circuits*, vol. 36, No. 7, pp. 1094-1100, 2001.

E. Chow, A. Chiebowski, and P. Irazoqui, "A miniature-implantable RF-wireless active glaucoma intraocular pressure monitor," *IEEE Trans. Biomed. CircuitsSyst.*, vol. 4, No. 6, pp. 340-349, 2010.

P. Chen, S. Saati, R. Varma, M. Humayun, and Y. Tai, "Wireless intraocular pressure sensing using microfabricated minimally invasive flexible-coiled LC sensor implant," *J. Microelectromechan. Syst.*, vol. 19, No. 4, pp. 721-734, 2010.

T. Eggers, J. Draeger, K. Hille, C. Marschner, P. Stegmaier, J. Binder, and R. Laur, "Wireless intra-ocular pressure monitoring system integrated into an artifical lens," in *Proc. 1 st Annu. Int. Conf Microtechnologies in Medicine and Biology*, 2000, pp. 466-469.

G. Chen, M. Fojtik, D. Kim, D. Fick, J. Park, M.Seok, M. Chen, Z. Foo, D. Sylvester, and D. Blaauw, "Millimeter-scale nearly perpetual sensor system with stacked battery and solar cells," in *IEEE Int. Solid State Circuits Con/ Dig. Tech. Papers* (ISSCC 2010), 2010, pp. 288-289.

A. Dosso, L. Cottet, N. D. Burgener, and S. Di Nardo, "Outcomes of coaxial microincision cataract surgery vs. conventional coaxial cataract surgery," *J. Cataract & Refractive Surgery*, vol. 34, No. 2, pp. 284-288, 2006.

K. Mansouri and T. Shaarawy, "Continuous intraocular pressure monitoring with a wireless ocular telemetry sensor: Initial clinical experience in patients with open angle glaucoma," *Brit. J. Ophthalmol.*, 2011.

A. Poon, S. O'Driscoll, and T. Meng, "Optimal operating frequency in wireless power transmission for implantable devices," in *Proc. 29th Annu. Int. Conf of the EEE Engineering in Medicine and Biology Society* (EMBS 2007), 2007, pp. 5673-5678.

S. O'Driscoll, A. Poon, and T. Meng, "A mm-sized implantable power receiver with adaptive link compensation," in *IEEE Int. Solid. State Circuits Conf Dig. Tech. Papers* (JSSCC 2009), 2009, pp. 294-295a.

J. Pandey and B. Otis, "A 90 µW MICS/ISM band transmitter with 22% global efficiency," in *Proc. 2010 IEEE Radio Frequency Integrated Circuits Symp.* (RFIC), May 2010, pp. 285-288.

J. Bohorquez, A. Chandrakasan, and J. Dawson, "A 350 µW CMOS MSK transmitter and 400 µW OOK super-regenerative receiver for medical implant communications," *IEEE J. Solid.State Circuits*, vol. 44, No. 4, pp. 1248-1259, Apr. 2009.

D. Yeager, F. Zhang, A. Zarrasvand, N. George, T. Daniel, and B. Otis, "A 9 µW, addressable GEN2 sensor tag for biosignal acquisition," *IEEE J. Solid.StateCircuits*, vol. 45, No. 10, pp. 2198-2209, Oct. 2010.

R. D. Freeman and I. Fatt, "Environmental influences on ocular temperature," *Investigat. Ophthalmol. Jlis. Sci.*, vol. 12, No. 8, pp. 596-602, Aug. 1973.

*IEEE Standard for Safety Levels With Respect to Human Exposure to Radio Frequency Electromagnetic Fields, 3 kHz to 300 GHz* IEEE Std. C95.I. 2006.

S. Kingman, "News—In Focus—Glaucoma is second leading cause of blindness globally," *Bulletin of the World Health Organization. Bulletin De L'Organisation Mondiale De La Sante*, vol. 82 (11), pp. 887-888, 2004.

Hughes, E., P. Spry, and J. Diamond, "24-hour monitoring of intraocular pressure in glaucoma management: A retrospective review," *American Journal of Ophthalmology*, 2004, 137 ( 1).

M. Leonardi, E.M. Pitchon, A. Bertsch, P. Renaud, and A. Mermoud, "Wireless contact lens sensor for intraocular pressure monitoring: assessment on enucleated pig eyes", *Acta Ophthalmo/ogica*, vol. 87, pp. 433-437, 2009.

L. Rosengren, P. Rangsten, Y. Baecklund, and B. Hoek, "A system for passive implantable pressure Sensors," *Sensors and Actuators. A, Physical*, vol. 43, pp. 55-58, 1994.

U. Schnakenberg, P. Walter, G. vom Bogel, C. Kruger, H. C. Ludtke-Handjery, A. H. Richter, W. Specht, P. Ruokonen, and W. Mokwa, "Initial investigations on systems for measuring intraocular pressure." *Sensors and Actuators. A, Physical*, vol. 85 (I), pp. 287-291, 2000.

Y. C. Shih, T. Shen and B. Otis, "A 2.3 µW Wireless Intraocular Pressure/Temperature Monitor", *IEEE Journal of Solid-State Circuits*, vol. 46 (II), pp. 2592-2601, 2011.

Shih et al. "A2.3 µW Wireless Intraocular Pressure/Temperature Monitor" Solid State Circuits Conference, Nov. 2010, pp. 1-4 [online] http://ieeexplore.ieee.org/stamp/stamp.jsp?tp=&arnumber=5716599.

\* cited by examiner

Table 1

| Material | Fabrication Process | Biocompatible | Young's Modulus (Mpa) | Elongation (%) | References |
| --- | --- | --- | --- | --- | --- |
| PDMS | Spin-coating and molding | USP* Class VI | < 0.9 | 600 | [27, 34-36] |
| Parylene-C | CVD and $O_2$ plasma | USP* Class VI | 20 | 200 | [28, 29, 37-39] |
| Polyimide | Spin-coating, photodefinable, wet etching and $O_2$ plasma | | 8830 | 30 | [31, 40, 41] |

*: United States Pharmacopeia

*FIG. 7*

Histogram of the antenna resistance measured over 150 bending cycles.

Table 2: Commercially available low temperature solders (data from Indium Corp.)

| Liquidus Temp. (°C) | Solidus Temp. (°C) | Elemental Composition (% by Mass) |
|---|---|---|
| 43 | 38 | 42.9Bi 21.7Pb 18.3In 8.0Sn 5.1Cd 4.0Hg |
| 47 | 47 | 44.7Bi 22.6Pb 19.1In 8.3Sn 5.3Cd |
| 52 | 47 | 44.7Bi 22.6Pb 16.1In 11.3Sn 5.3Cd |
| 56 | 54 | 49.1Bi 20.9In 17.9Pb 11.6Sn 0.5Cd |
| 58 | 58 | 49.0Bi 21.0In 18.0Pb 12.0Sn |
| 60 | 60 | 51.0In 32.5Bi 16.5Sn |
| 62 | 62 | 61.7In 30.8Bi 7.5Cd |
| 65 | 57 | 47.5Bi 25.4Pb 12.6Sn 9.5Cd 5.0In |

*FIG. 14*

INTRAOCULAR PRESSURE SENSING DEVICES AND ASSOCIATED SYSTEMS AND METHODS

CROSS-REFERENCE TO RELATED APPLICATIONS

This application claims the benefit of U.S. Provisional Patent Application No. 61/701,511, filed Sep. 14, 2012, which is incorporated herein by reference in its entirety.

TECHNICAL FIELD

The present technology is generally related to intraocular pressure sensing devices and associated systems and methods. In particular, several embodiments are directed to continuous intraocular pressure monitoring devices.

BACKGROUND

Glaucoma is a group of eye conditions resulting in damage to the optic nerve. The World Health Organization has identified glaucoma as the second leading cause of blindness in the world. It is estimated that glaucoma was the cause of blindness in 8.4 million people globally in 2010, rising to 11.2 million by 2020. Increase in intraocular pressure ("IOP"), or fluid pressure within the eye, is considered to be one of the factors that cause glaucoma. IOP levels normally range from 10 mmHg to 21 mmHg, but can be up to 50 mmHg in a diseased eye. Early diagnosis and treatment of abnormally high IOP can minimize or prevent optic nerve damage and limit glaucoma-related vision loss. Conventionally, IOP is measured by tonometry, which requires an ophthalmologist visit. As a result, several months may pass between IOP measurements, which is far less frequent than known circadian fluctuations of IOP. Moreover, glaucoma can be a painless disease that progresses gradually over a long time period, typically rendering it unnoticeable until a loss of vision or irreversible nerve damage occurs. Early diagnosis and treatment can minimize or prevent such a result.

Conventional devices directed towards continuous IOP monitoring suffer from several drawbacks. For example, many conventional devices require surgery (e.g., implanting the IOP sensing device in the anterior chamber of the eye, embedding the IOP sensing device in an implantable prosthetic lens, etc.). On the other hand, many non-invasive conventional devices measure pressure indirectly and thus are inherently inaccurate. For example, one such conventional device includes an IOP sensing device embedded within a contact lens. Pressure is measured indirectly by corneal curvature as measured by a strain gauge. The accuracy of the IOP measurements, however, are affected as a result of variation of the cornea thickness and diameter.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIG. 7 is a table of polymers.

FIG. 14 is a table of solder materials.

DETAILED DESCRIPTION

The present technology is generally directed to devices, systems, and methods for wireless monitoring of IOP. In one embodiment, for example, an IOP monitoring system includes an implantable intraocular assembly and an external unit configured to be positioned at an external location. The external unit can be configured to transmit power to and receive data from the intraocular assembly. The intraocular assembly can include an IOP sensing device embedded within a flexible, expandable annular member. The IOP sensing device can include an antenna, a pressure sensor, and a microelectronic device encapsulated by an elastomer.

Specific details of several embodiments of the present technology are described herein with reference to FIGS. 3-17F. Although many of the embodiments are described below with respect to devices, systems, and methods for wirelessly monitoring IOP, other pressure sensing applications are within the scope of the present technology (e.g., non-eye related pressure sensing, temperature sensing, etc.). Additionally, other embodiments of the present technology can have different configurations, components, or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Generally, unless the context indicates otherwise, the terms "anterior" and "posterior" within this disclosure reference a position relative to the front and back of a patient's body, respectively. For example, "anterior" can refer to a position closer to the front of the eye, and "posterior" can refer to a position that is closer to the back of the eye.

I. Relevant Anatomy

Figure 1A:
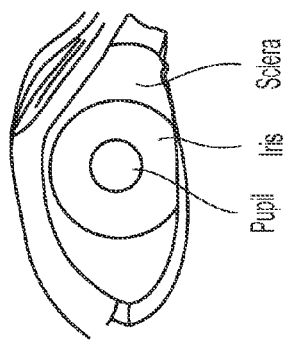
FIG. 1A is a front view of a human eye.
Figure 1B:
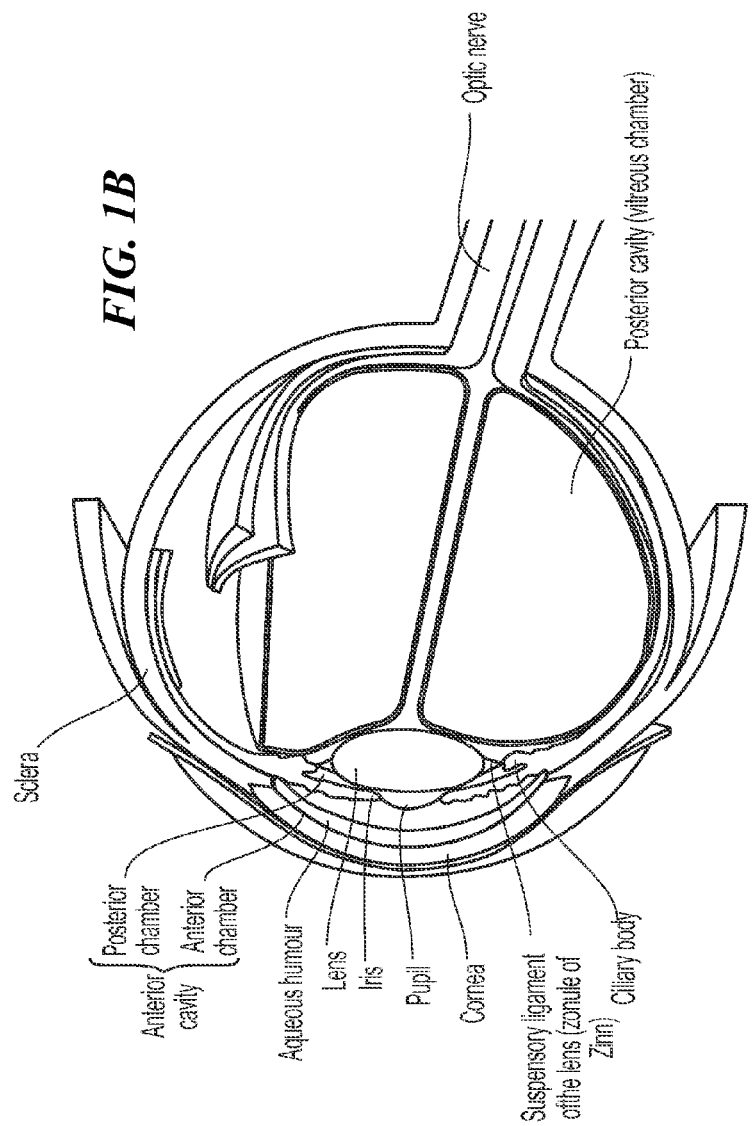
FIG. 1B is a schematic side cross-sectional front view of the eye in FIG. 1A.

FIG. 1A is a schematic front view of a human eye, and FIG. 1B is a schematic partial cross-sectional side view of the eye as isolated from the rest of the facial anatomy. Referring to FIGS. 1A and 1B together, the eye can generally be divided into anterior and posterior cavities with the lens in between. The anterior cavity can further be divided into the anterior chamber (between the cornea's innermost surface and the iris) and the posterior chamber (between the iris and the zonule of Zinn), as shown in the enlarged view of FIG. 1C.

Figure 1C:
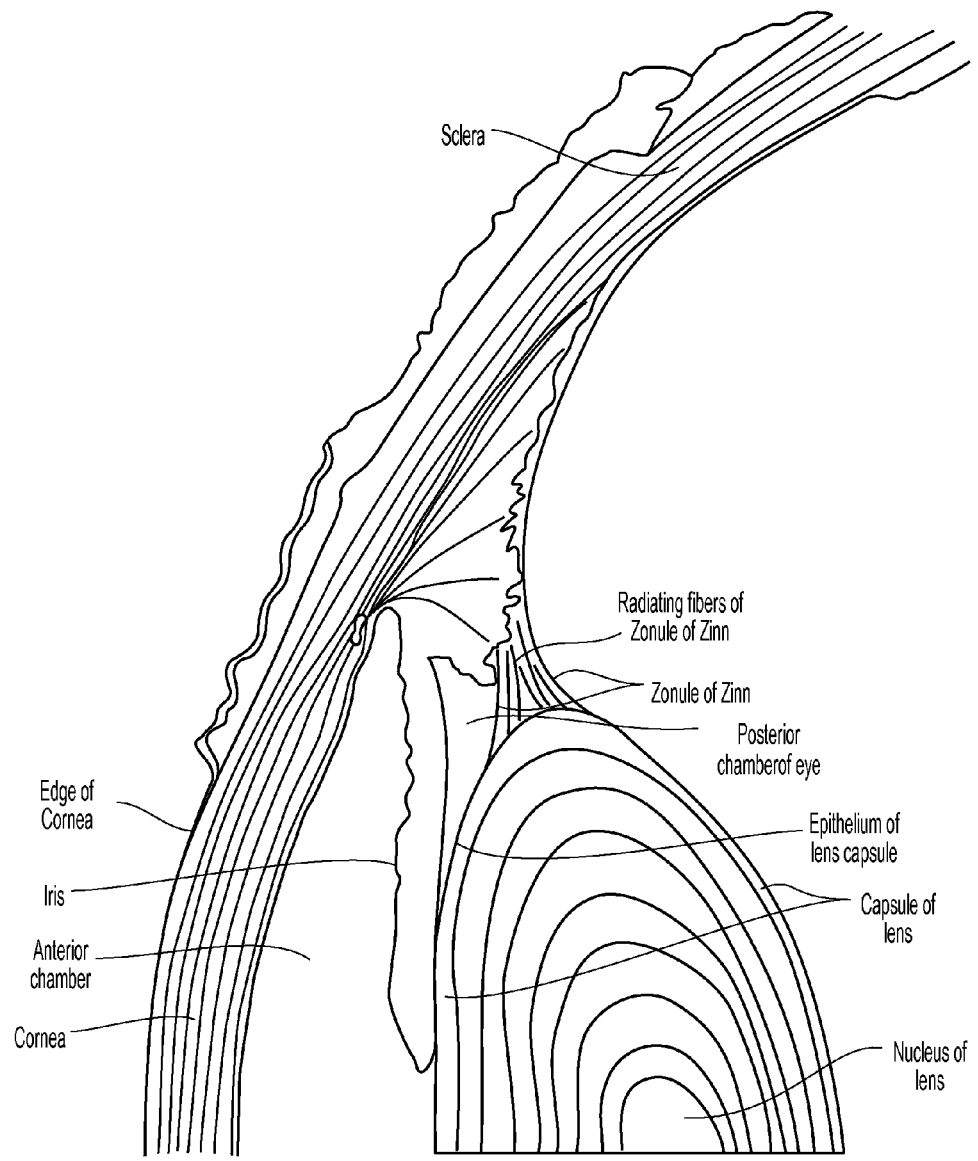
FIG. 1C is an enlarged schematic illustration of an anterior portion of the eye.

Referring still to FIG. 1C, the lens is held in place by zonular fibers which connect the capsular bag to the ciliary body. The capsular bag is a smooth, elastic collagen membrane that completely surrounds the lens. The lens fibers form the bulk of the interior of the lens. Because of its elasticity, the capsule causes the lens to assume a more globular shape when not under the tension of the zonular fibers. The capsule varies from 2-28 μm in thickness, being thickest near the equator and thinnest near the posterior pole.

A cataract is a painless, cloudy area in the lens of the eye that blocks light from reaching the nerve layer in the posterior cavity. Cataract surgery separates the cataract from the capsular bag. In most cases, the lens will be replaced with an IOL.

Figure 2A:
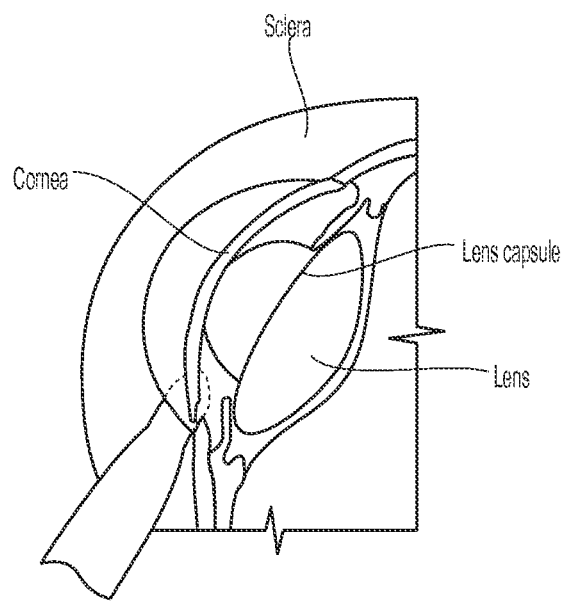
FIGS. 2A-2D illustrate a method for implanting an intraocular lens ("IOL") and/or capsular tension ring in accordance with embodiments of the present technology
Figure 2B:
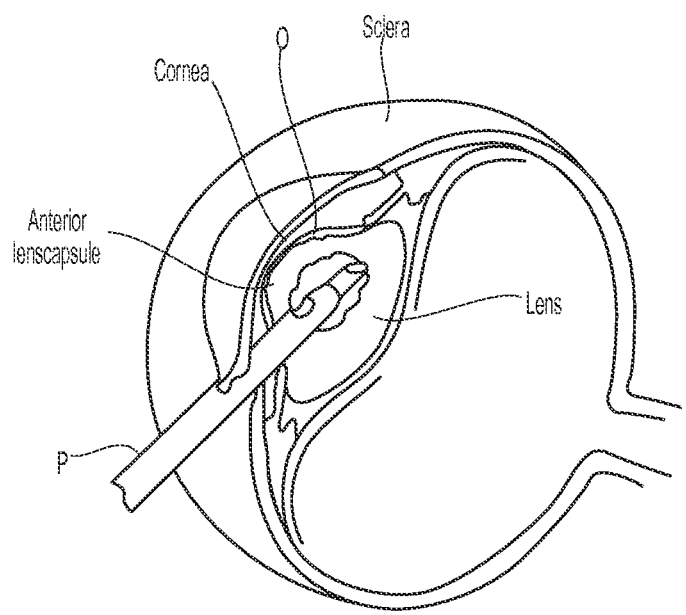
Figure 2C:
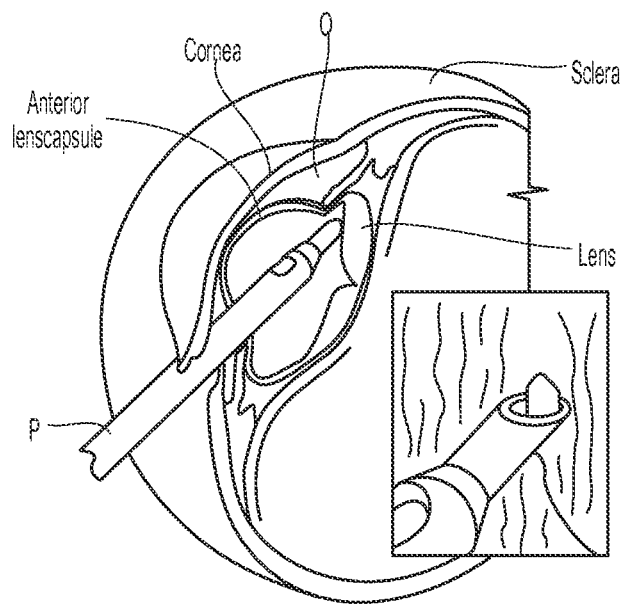

Phacoemulsification is a minimally invasive method for removing the cataract as well as the anterior portion of the capsular bag. The posterior portion of the capsular bag is left inside the eye for several reasons, one being to support and secure the IOL. As shown in FIG. 2A, a clinician (not shown) makes an incision (e.g., between about 1 mm to about 3 mm) in the eye where the cornea meets the sclera. Next, a small, circular opening O is made in the anterior portion of the capsular bag and a phacoemulsification probe P is inserted into the eye (FIG. 2B). The probe P emits ultrasound energy to break the cataract into small pieces. As shown in FIG. 2C, the clinician then uses suction to remove the cataract and lens pieces from the eye.

Figure 2D:
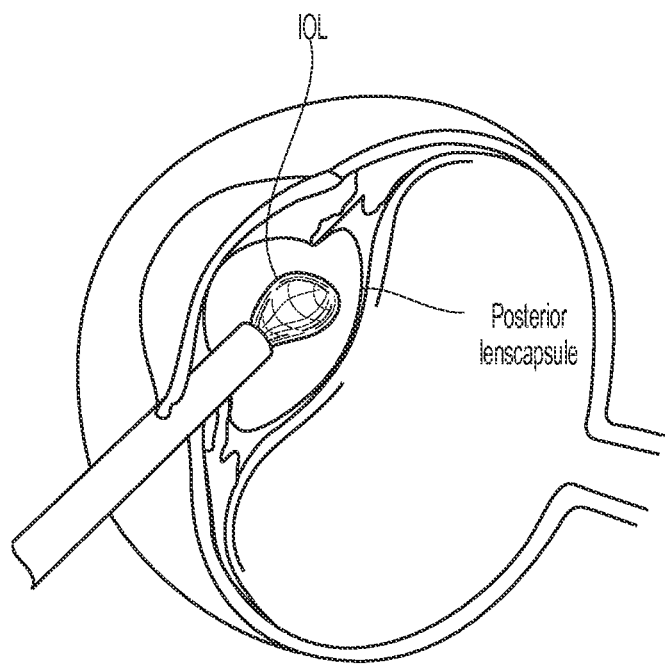

After the cataract and/or natural lens has been removed, the IOL is positioned inside the capsular bag (FIG. 2D). The IOL is folded within the introducer for delivery to the capsular bag and is delivered through the same incision used for the phacoemulsification. Once released, a portion of the IOL exerts an outward force on the inner walls of the capsular bag, thereby securing the IOL.

Figure 3:
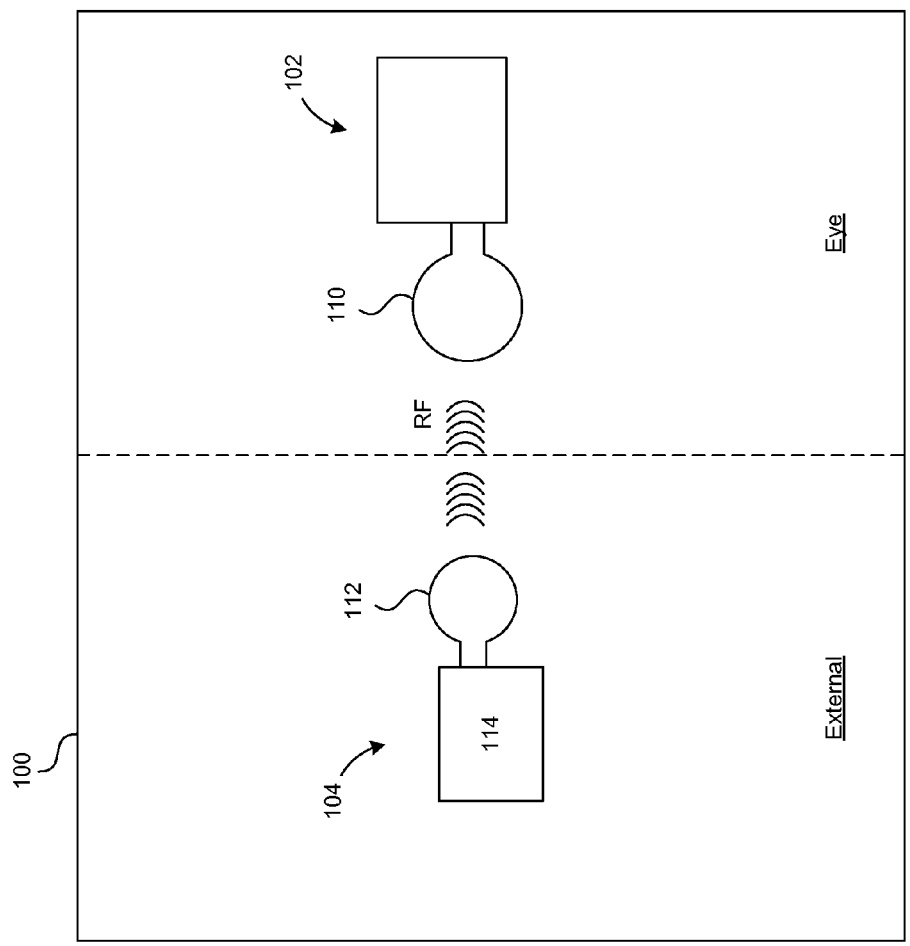
FIG. 3 is a schematic representation of an intraocular pressure monitoring system configured in accordance with an embodiment of the present technology.

II. Selected Embodiments of Intraocular Pressure Monitoring Systems and Assemblies FIG. 3 is a schematic representation of an IOP monitoring system 100 ("system 100") configured in accordance with an embodiment of the present technology. The IOP monitoring system 100 can include an intraocular assembly 102 ("assembly 102") configured for implantation in an eye of a human patient and an external unit 104 configured to be positioned at a location external to the patient. In some embodiments, for example, the external unit 104 may be configured to be removably attached to the patient's clothing or body. In other embodiments, however, the external unit 104 may have a different arrangement relative to the patient. The intraocular assembly 102 is configured to wirelessly communicate with the external unit 104 for power and data transmission.

As shown in FIG. 3, the external unit 104 can include an antenna 112 (e.g., a coil antenna) and memory and processing circuitry 114. To communicate with the intraocular assembly 102, the antenna 112 can be configured to send radiofrequency ("RF") waves to the implantable assembly 102. The antenna 112 can also be configured to receive a frequency-encoded signal from the assembly 102 via RF backscatter. For example, the antenna 112 can receive intermediate frequency modulation data from the implantable assembly 102 and the memory and processing circuitry 114 can perform further signal processing to obtain a measured data sample. The external unit 104 can further perform power delivery, FM demodulation, digitalization, data storage, sampling duty cycle, channel monitoring and selection and/or other suitable functions.

Figure 4A:
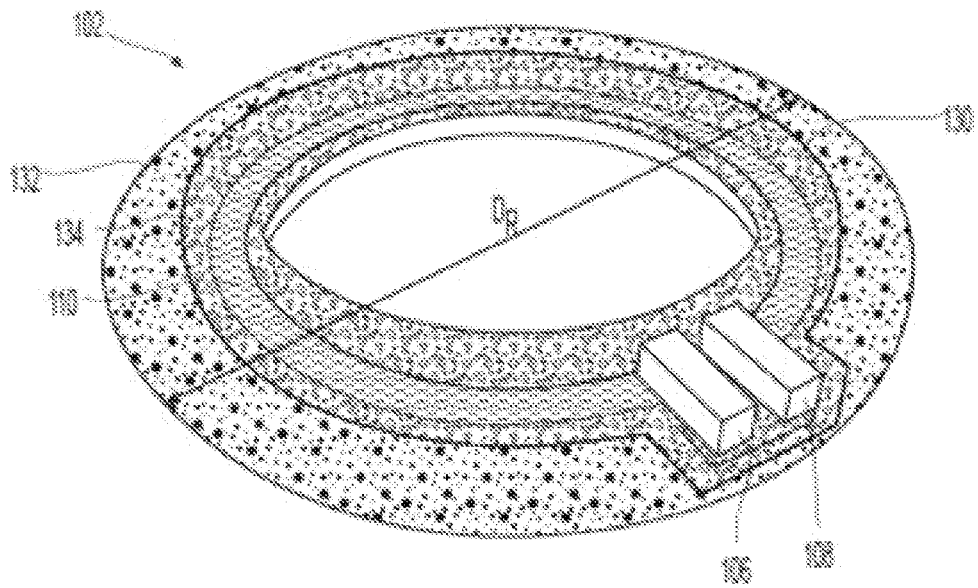
FIG. 4A is a partially schematic perspective view of an intraocular assembly configured in accordance with an embodiment of the present technology.
Figure 4B:
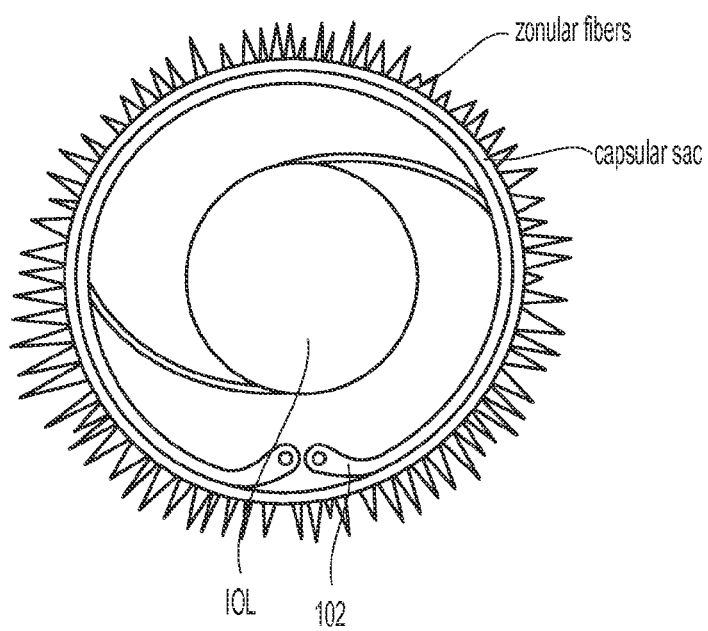
FIG. 4B is a front view of the intraocular assembly of FIG. 4A implanted within a human eye in accordance with an embodiment of the present technology.

FIG. 4A is a partially-schematic perspective view of the intraocular assembly 102 in an expanded configuration, and FIG. 4B is a front view of the intraocular assembly 102 implanted within the eye together with an IOL. In some embodiments, the intraocular assembly 102 may be implanted without subsequent implantation of an IOL. Referring to FIGS. 4A and 4B together, the assembly 102 includes an IOP sensing device 130 embedded within a flexible annular member 132. Although FIG. 4A shows an annular member 132 having a closed ring-like structure, in other embodiments the annular member 132 may have an opening along its circumference.

Since the annular member 132 comprises the outermost structure of the intraocular assembly 102, the shape and size of the intraocular assembly 102 are defined by the shape and size assumed by the annular member 132. The circular shape of the annular member 132 allows the IOP sensing device 130 to be embedded within the capsular bag without impeding the patient's vision. In some embodiments, the annular member 132 can be torus-shaped with a major radius between about 4 mm and about 7 mm, and a minor radius between about 1 mm and about 2 mm. For example, in particular embodiments, the annular member 132 can have a major radius between about 5.5 mm and about 6.0 mm, and a minor radius between about 1.3 mm and 1.4 mm. Likewise, as shown in FIG. 4B, once implanted the annular member 132 and/or assembly 102 can have an outer diameter $D_R$ between about 10 mm and about 15 mm. In some embodiments, the outer diameter $D_R$ can be between about 12 mm and about 13 mm. In other embodiments, the annular member 132 may have a different shape and/or different dimensions.

The annular member 132 can be made of a flexible material capable of being compressed (e.g., folded, squeezed, collapsed, etc.) for delivery through an incision between about 1 mm to about 4 mm long (e.g., between about 2 mm and about 3 mm, about 2.6 mm, etc.). In one particular embodiment, for example, the annular member 132 and/or assembly 102 can have a compressed cross-sectional area of about 2 mm by 1 mm. In some embodiments, the annular member 132 can include one or more materials, such as poly(ether urethane) ("PEU") having shape memory properties that expand in response to fluid exposure. For example, the annular member 132 can be dehydrated and compressed for delivery. Once exposed to the fluid within the eye, the annular member 132 can transform from the compressed, delivery state to an expanded, torus shape as the annular member 132 takes on a fluid volume. The polymer composition of the annular member 132 can be tailored to achieve a resilience time of about 1.5 second to about 5.0 seconds. As referred to herein, "resilience time" is the time required for the dehydrated, compressed annular member 132 to relax or expand to its circular shape when submerged in a fluid. Once expanded, the annular member 132 can help preserve the shape of the capsular bag and stabilize weakened, broken or missing zonules that normally support the lens.

Figure 5:
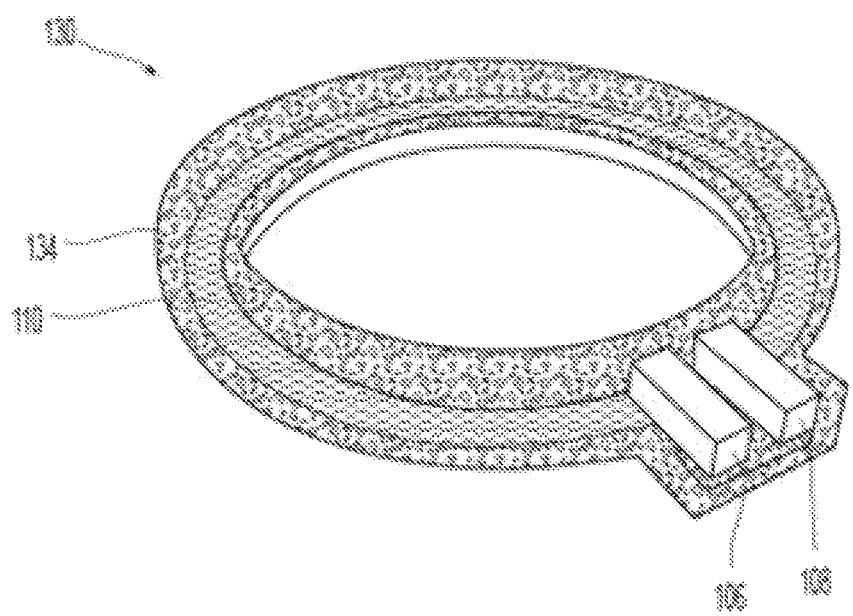
FIG. 5 is a partially schematic perspective view of an intraocular pressure sensing device configured in accordance with an embodiment of the present technology.

Referring now to the isolated view of the IOP sensing device 130 in FIG. 5 (before implantation into the eye of the patient), the device 130 can include a pressure sensor 108 and a low-power microelectronic structure 106 in electrical connection with an antenna 110. The pressure sensor 108, microelectronic structure 106, and antenna 110 can be encapsulated by an encapsulant 134. In some embodiments, the IOP sensing device 130 may also optionally include a temperature sensor (not shown). The pressure sensor 108 can be a capacitive MEMS pressure sensor (e.g., E1.3N, microFAB Bremen GmbH, Germany). Changes in intraocular pressure cause a change in capacitance in the pressure sensor 108. The change in capacitance is communicated to the microelectronic structure 106, and the microelectronic structure 106 converts the change in capacitance to a change in frequency via a low power relaxation oscillator (described below with reference to FIG. 6). This frequency-encoded signal is subsequently transmitted from the intraocular assembly 102 to the external unit 104 via RF backscatter. Compared to conventional systems using wirelessly-powered active transmitters, the use of RF backscatter (e.g., passive telemetry) in the present technology is expected to significantly reduce the size of the implantable assembly 102 as well as the RF energy exposure of the tissue. For example, backscatter communication for up-link communication avoids the need for an RF oscillator and active transmitter within the implantable assembly 102. By encoding data using analog IF modulation, circuit complexity and communication protocol overhead in the implantable assembly 102 are reduced since an analog-to-digital converter and data packetization logic are not needed. Likewise, the present technology shows a significant reduction (e.g., 150 µW~1.1 mW) in active power dissipation compared to conventional devices having on-chip digitalization circuitry and/or active transmitters.

Figure 6:
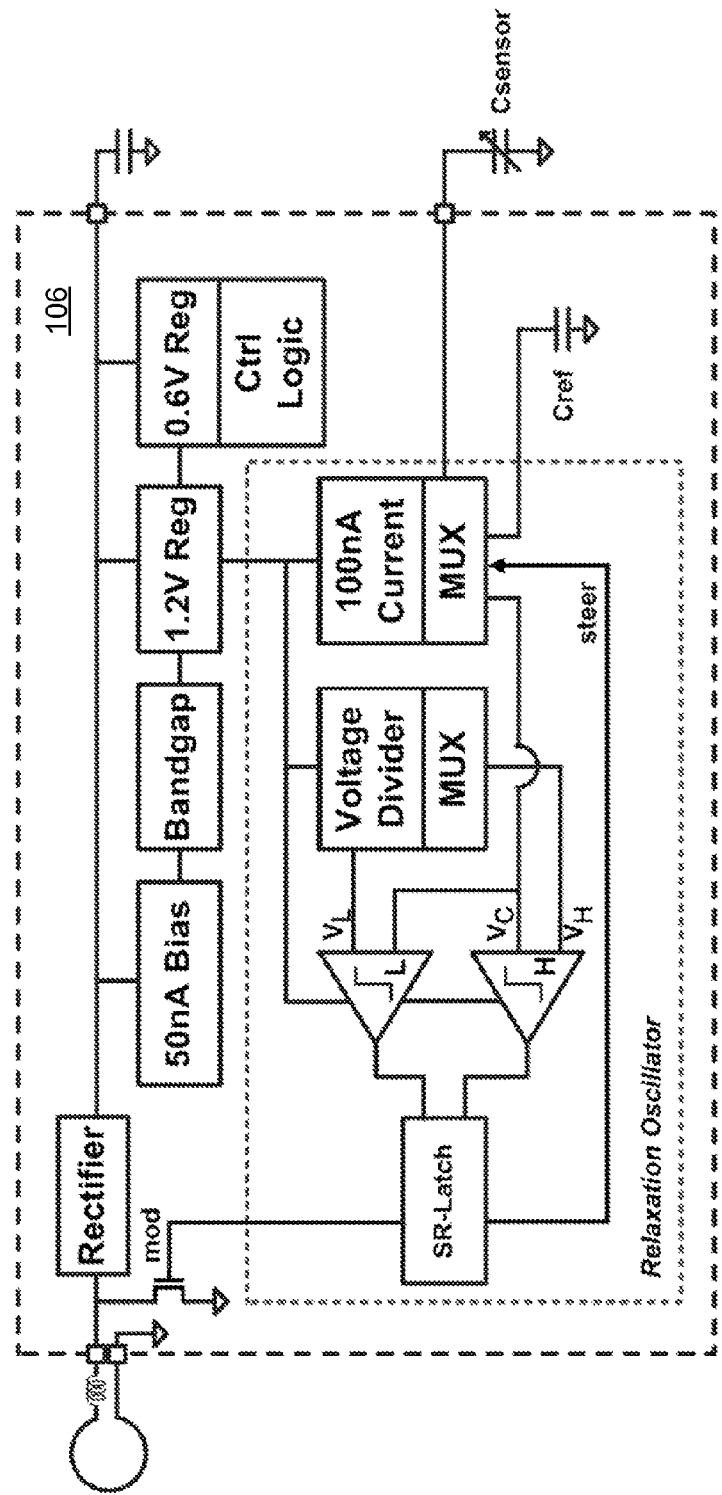
FIG. 6 is a block diagram of a microelectronic device configured in accordance with an embodiment of the present technology.
Figure 8:
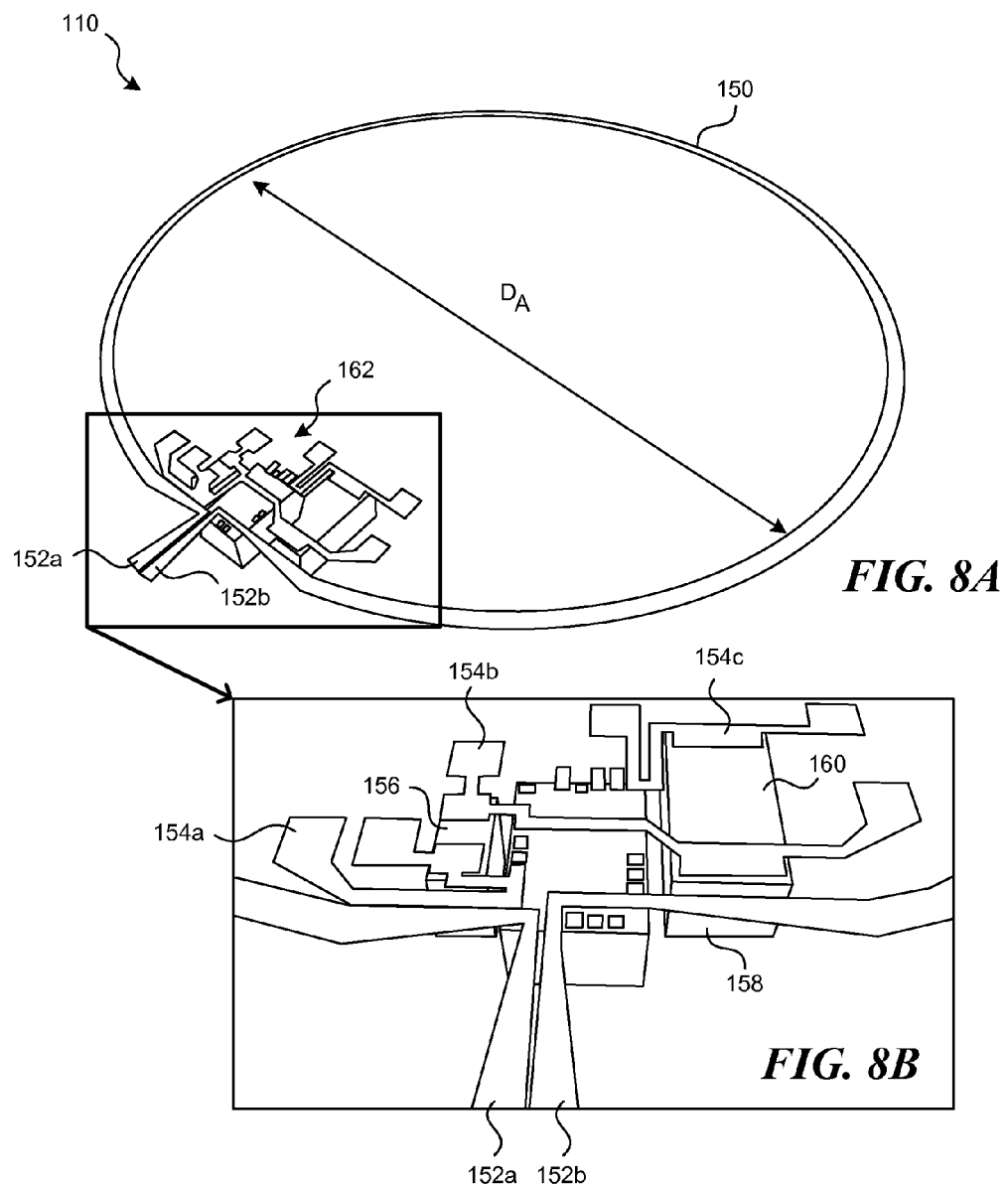
FIG. 8A is a perspective view of an antenna and associated circuitry configured in accordance with an embodiment of the present technology.
FIG. 8B is an enlarged view of a portion of the antenna and associated circuitry of FIG. 6A configured in accordance with an embodiment of the present technology.

FIG. 6 illustrates a block diagram of an embodiment of the microelectronic device 106 configured in accordance with the present technology. The microelectronic device 106 operates under low-power conditions (e.g., about 2.3 µW) and can be wirelessly powered by RF energy provided by the external unit 104 operating at about 2.4 GHz. In contrast with embodiments of the microelectronic device 106, many conventional intraocular device designs use inductive coupling in the kHz to MHz range, requiring a large, multi-turn coil inductor in the implant. Larger device size also requires a larger incision in the patient, which necessitates stitches and also prolongs wound recovery time.

As shown in FIG. 6, the microelectronic device 106 can include a rectifier for RF power transfer, a relaxation oscillator for C-to-F and temperature-to-frequency conversion, and a backscatter modulator for up-link communication. In some embodiments, the microelectronic device 106 can have gold (Au) electrical connection pads, which have stronger bonding with the metal alloy used for the antenna 110. In other embodiments, however, other alloys may be used. Additional details on this and other suitable microelectronic devices can be found in Shih, Y. C., B. P. Otis, and T. Shen, "A 2.3 uW wireless intraocular pressure/temperature monitor," IEEE J Solid State Circuits IEEE Journal of Solid-State Circuits, 2011 46(11) pp. 2592-2601, which is incorporated by reference herein in its entirety.

Referring back again to FIG. 5, the encapsulant 134 can have a generally circular shape and is configured to serve as a protective layer for the antenna 110. Also, the encapsulant 134 can serve as the substrate when forming the antenna 110 and the microelectronic structure 106. In particular embodiments, the encapsulant 134 may include polydimethylsiloxane ("PDMS"). PDMS is biocompatible, chemically inert, and has a relatively low Young's modulus. As a result, at least in embodiments of the present technology where the annular member 132 is made of PEU, a PDMS encapsulant 134 will not interfere with the shape-memory capability of the annular member 132. A comparison of PDMS with parylene-C and polyimide, two common polymers in flexible electronics, is presented in the table in FIG. 7. As shown in the table of FIG. 7, both parylene-C and polymide have various drawbacks for use in the present application. For example, both polyimide and parylene-C have higher Young's moduli compared to PDMS, and polyimide is not certified as a biocompatible implant material. Also, both materials are exposed to chemicals during the photolithography process used for metal patterning, which can increase the risk of long term low-toxicity since parylene-C and polyimide have moisture absorption rates of 0.06% and 0.8-1.4% respectively.

Figure 9:
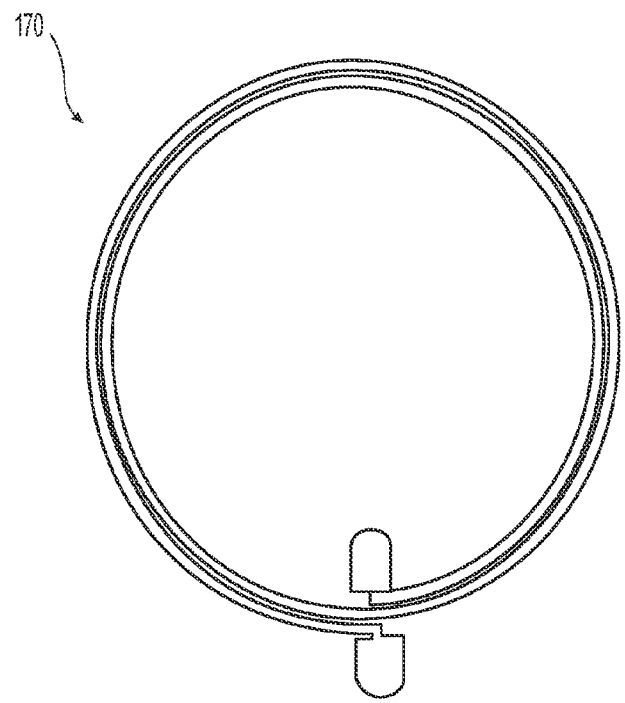
FIG. 9 is a two-turn antenna configured in accordance with an embodiment of the present technology.
Figure 10:
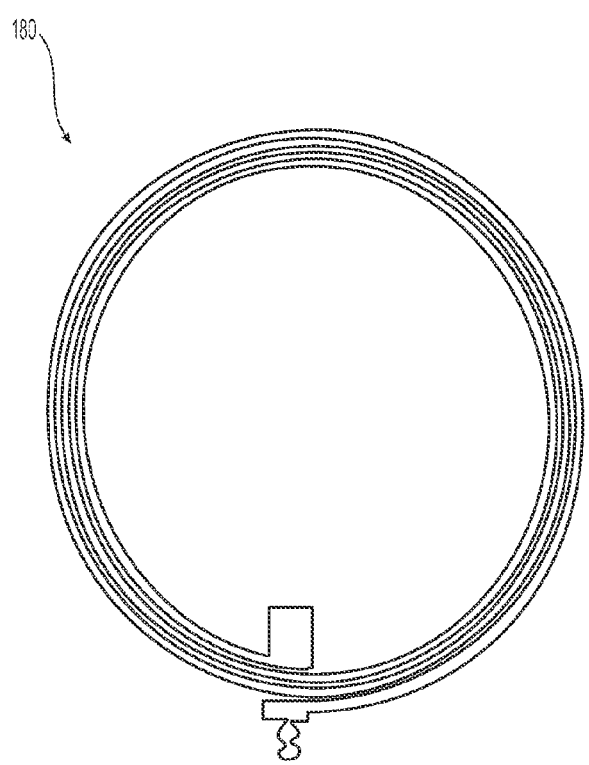
FIG. 10 is a three-turn antenna configured in accordance with an embodiment of the present technology.

FIG. 8A shows one embodiment of an IOP sensing device 130 configured in accordance with the present technology with the encapsulant 134 (FIG. 5) removed for purposes of illustration. As shown in FIG. 8A, the antenna 110 can be a single-turn loop antenna. In other embodiments, however, the antenna 110 may have more than one turn to increase power transmission efficiency. FIG. 9, for example, illustrates an embodiment of a two-turn loop antenna 170, and FIG. 10 illustrates yet another embodiment of an antenna 180 with three turns.

Referring back to FIG. 8A, the intraocular assembly 102 is configured to receive RF electromagnetic energy from the external unit 104 (FIG. 3) via the antenna 110. The antenna 110 can have a generally circular shape with a circular body 150 and two legs 152 (labeled individually as legs 152a and 152b) that extend radially outwardly from the circular body 150. In some embodiments, the circular body 150 can have a diameter between about 0.90 cm and about 1.10 cm (e.g., about 1 cm). In particular embodiments, the circular body can have a width of about 200 µm and a height of about 35 µm. As described in greater detail below with respect to FIG. 11G, the legs 152a and 152b can individually correspond to openings 208 in a mold used to deliver solder during fabrication of the antenna. As such, the legs 152a and 152b can optionally be removed from the antenna 110 after fabrication.

FIG. 8B is an enlarged view of a plurality of interconnections 162 shown in FIG. 8A that electrically connect the microelectronic device 106, pressure sensor, temperature sensor, and/or electronic components. In the illustrated embodiment, the sensing device 130 includes three interconnections 154a, 154b, and 154c that electrically connect a first 156, second 158, and/or third electronic structure 160. For example, the first interconnection 154a can electrically connect the first electronic structure 156 to a second electronic structure 158, the second interconnection 154b can electrically connect the first, second and third electronic structures 156, 158, 160, and the third interconnection 154c can connect the second 158 and third 160 electronic structures. In other embodiments, the interconnections 162 may include different features and/or have a different arrangement.

Figure 11:
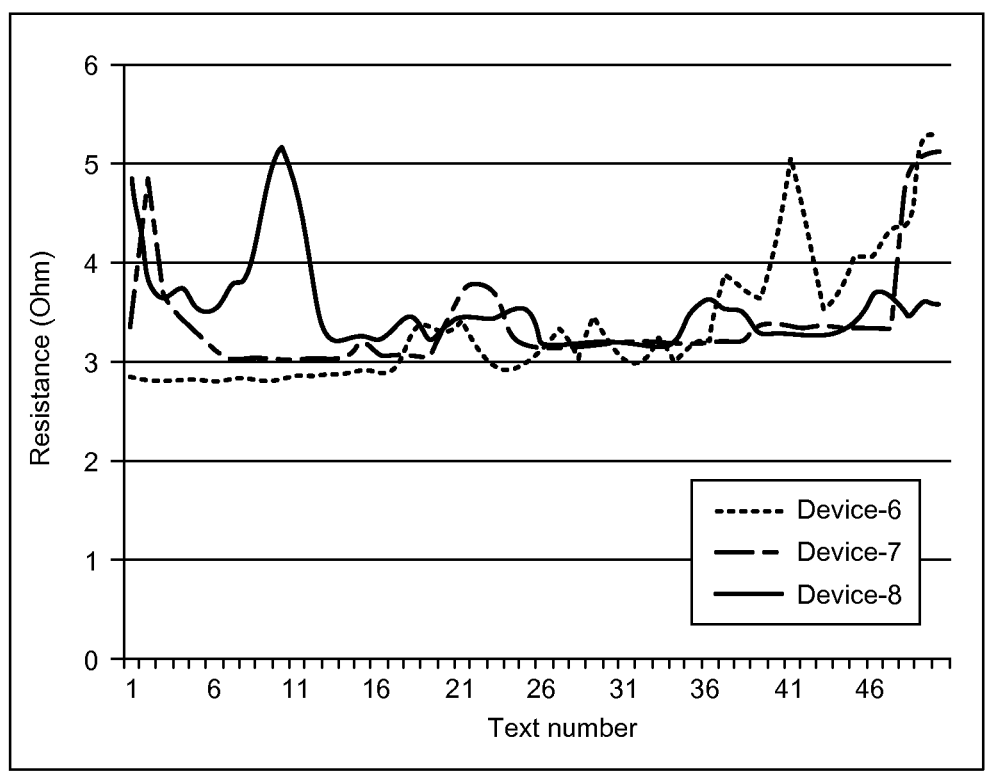
FIG. 11 is a graph of the antenna resistance measure over 50 bending cycles.
Figure 12:
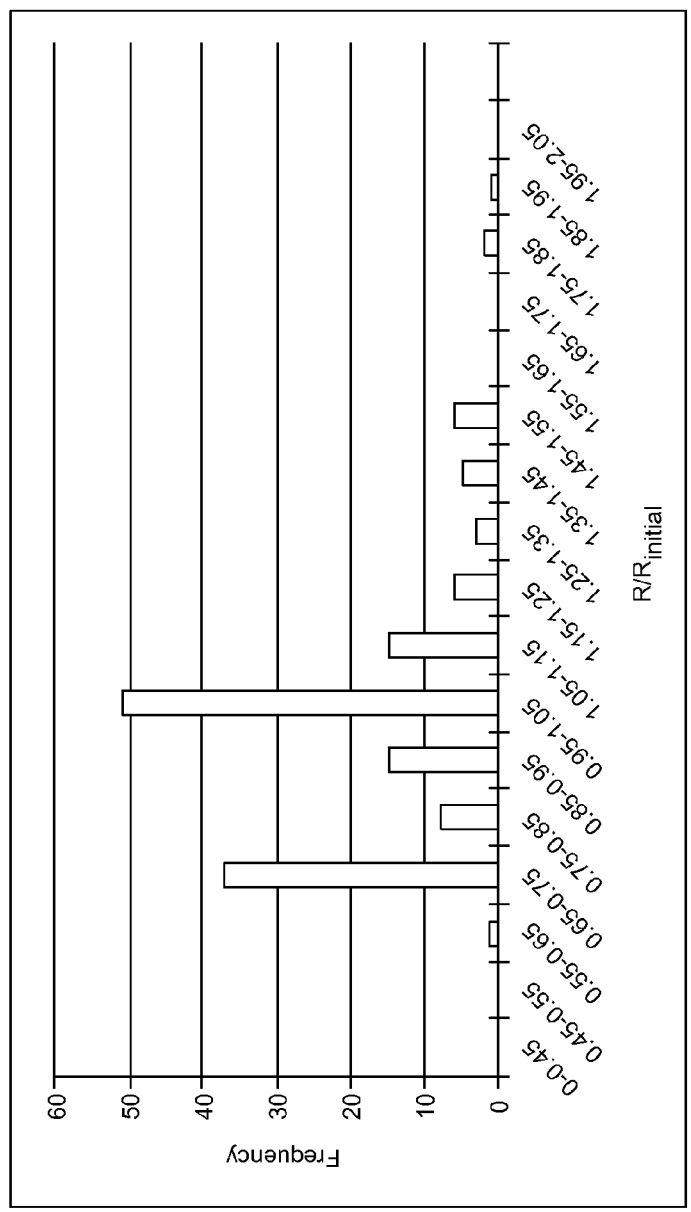
FIG. 12 is a histogram of the antenna resistance measured over 150 bending cycles.

As described in greater detail below with reference to FIGS. 17A-17E, the intraocular assembly 102 can experience harsh mechanical conditions during device implantation. Thus, it is important to ensure that the antenna 110 does not lose its electrical conductivity after implantation. FIG. 11, for example, shows the effect of applied stress on resistance for the assembly 102 when bent with respect to an initial position and relaxed back to the initial state. The histogram of the measured values is plotted with respect to an initial resistance in FIG. 12. Both plots illustrate that resistance fluctuates around the initial value. In other words, on average the antenna 110 resistance can vary between about 2.7Ω and 3.1Ω, both of which are below the 5Ω limit required for efficient RF power reception. Since the final implantable device will go through the process of folding and unfolding only once, 50 bending cycles provide enough confidence for its flexibility.

III. Selected Embodiments of Iop Sensing Devices and Methods of Fabrication

Figure 13A:
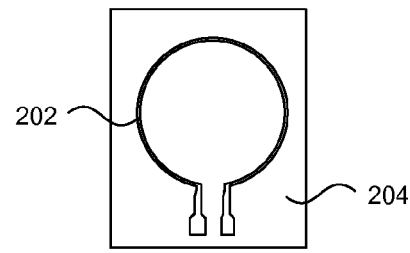
FIGS. 13A-13G illustrate a method for fabricating an antenna in accordance with embodiments of the present technology.
Figure 13B:
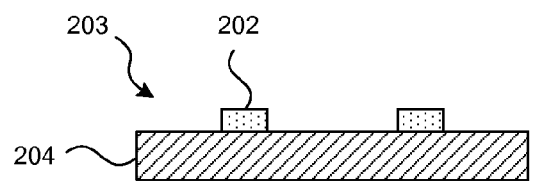

FIGS. 13A-13G illustrate a method for fabricating an antenna (e.g., the antenna 110) in accordance with embodiments of the present technology. FIGS. 13A and 13B, for example, are top and front views, respectively, of an intermediate structure 203 including a patterned photoresist material 202 formed on a substrate 204 (e.g., silicon (Si)) by photolithography or other methods known in the art. As shown in FIG. 13A, the photoresist material 202 can be patterned to define a desired antenna configuration, such as an open ring or horseshoe-shaped configuration as shown in the illustrated embodiment. In some embodiments, the ring-shaped photoresist material can have a mean radius between about 5 mm to about 6 mm (e.g., 5.75 mm), a width between about 195-205 µm (e.g., 200 µm) and a height between about 30 µm to about 40 µm (e.g., 35 µm). In other embodiments, the photoresist can have other suitable shapes and configurations. For example, the photoresist may be patterned to provide for one or more interconnections 162 for the one or more electrical components, as described above with reference to FIGS. 8A and 8B.

Figure 13C:
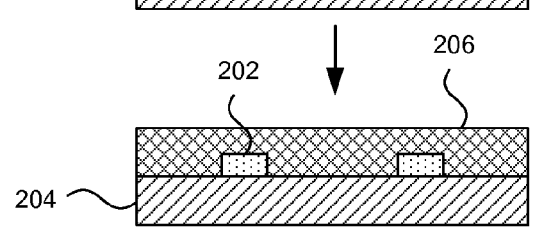
Figure 13D:
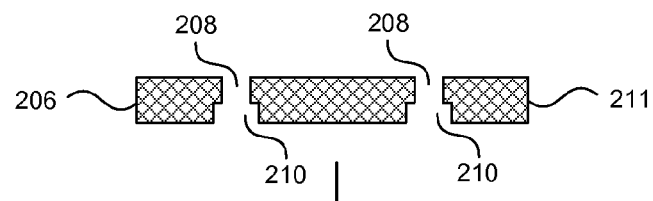

As shown in FIG. 13C, a first polymer material 206 (e.g., PDMS) can be formed on the substrate 204 and on the photoresist material 202. For example, the first polymer material 206 may be formed by spin-coating to a desired thickness (e.g., about 130 µm to about 150 µm). The first polymer material 206 may optionally be degassed under vacuum (e.g., about 300 Torr or less) for a desired time (e.g., about one hour) and heat-cured. In one particular embodiment, for example, the heat curing can be at about 70° C. for 30-40 minutes. Once solidified, the first polymer material 206 can be detached from the intermediate structure 203, leaving a ring-shaped indentation 210 within the first polymer material 206 (FIG. 13D). Openings 208 can be formed through the first polymer material 206 for solder delivery (e.g., about 0.5 mm to about 1.5 mm in diameter, about 1 mm in diameter, etc.) (see also FIG. 13G). In some embodiments, additional openings can be formed in the first polymer material 206 that correspond to microchannels for integration of the electronic components. This eliminates the need of wire-bonding, which may cause fracture under stress.

Figure 13E:
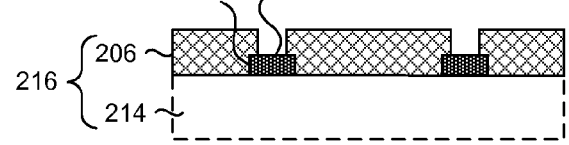

As shown in FIG. 13E, a second polymer material 214 (e.g., PDMS) (shown in phantom lines for purposes of illustration) is then bonded to a surface 211 of the first polymer material 206 adjacent the ring-shaped indentation 210 to form the floor of the microchannel(s), including the ring-shaped microchannel 218. In some embodiments, bonding between the first and second polymer materials 206, 214 may be achieved by $O_2$ plasma treatment (e.g., at about 27 W for about one minute). The second polymer material 214 can be formed on a substrate using the same techniques utilized in during formation of the first polymer material 206. In some embodiments, the second polymer material 214 can include an embedded PCB (not shown).

Before solder delivery to the microchannel(s) 218, the microchannel(s) 218 can optionally be surface-treated 220 to enhance interaction between the polymer mold 216 and the solder. In some embodiments, the surface treatment may consist of a one or more surface treatment agents, such as tridecafluoro-1,1,2,2-tetrahydrooctyl-1-trichlorosilane (e.g., applied under vacuum for at least 30 minutes). Additionally, surface treatment 220 may include application of a 10:1 PDMS mixture via spin-coating, and/or a droplet of 3-mercaptopropyltrimethoxysilane solution (0.1M solution prepared in acetonitrile) to the microchannel(s) 218.

Figure 13F:
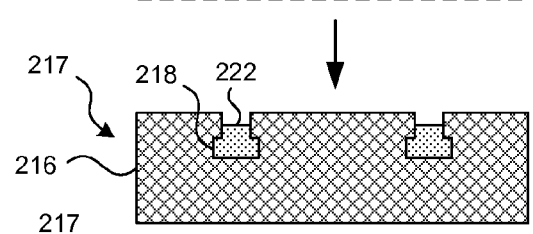
Figure 13G:
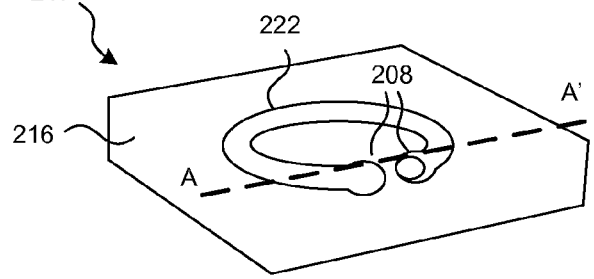
Figure 15:
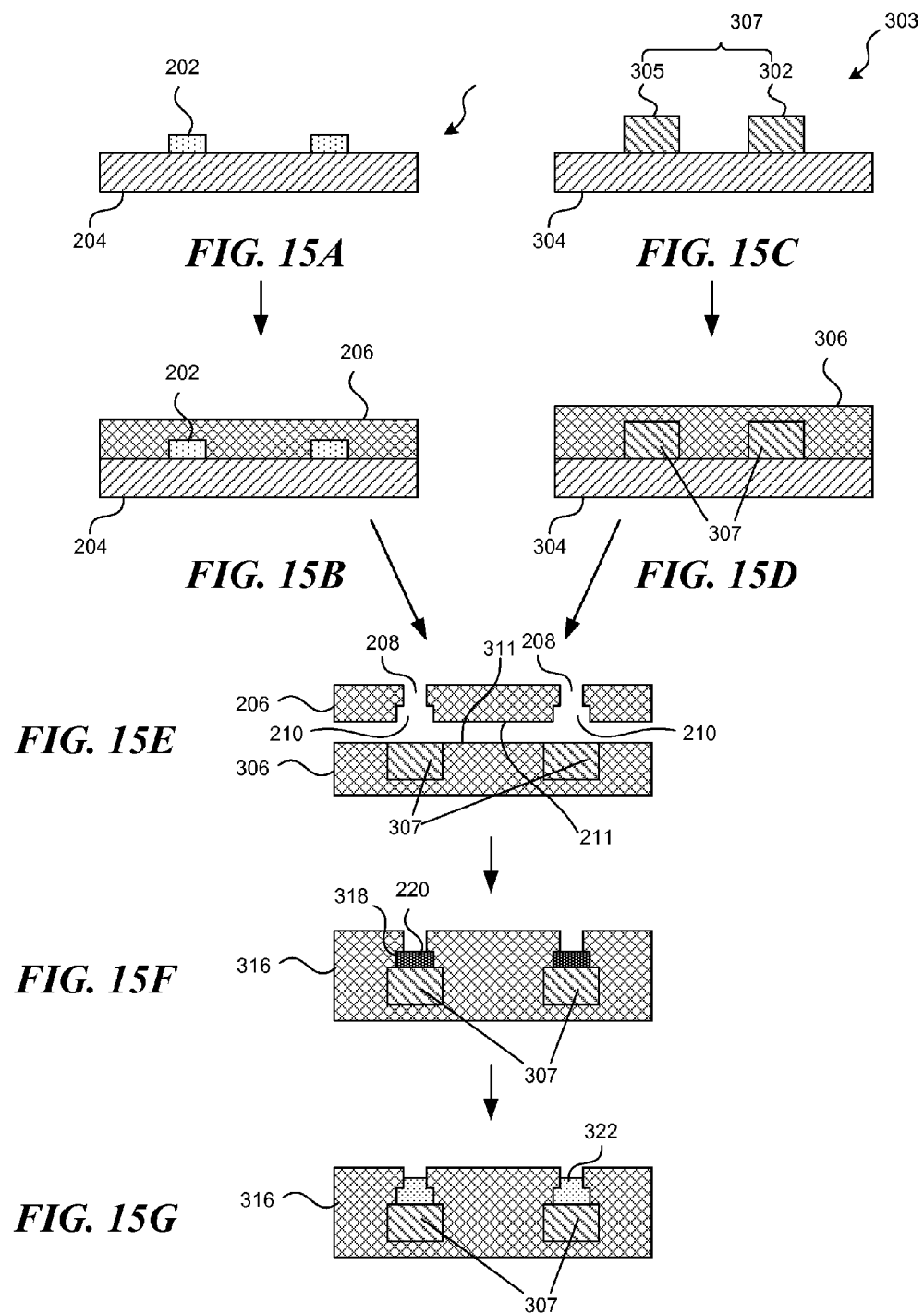
FIGS. 15A-15G illustrate a method for fabricating an IOP sensing device in accordance with embodiments of the present technology.

FIGS. 13F and 13G show front and top views, respectively, of an intermediate structure 217 after solder delivery to the microchannel(s) 218. Before solder delivery, the dried polymer mold 216 can be heated to 75° C., above the melting point of the solder. A droplet of liquid solder is delivered to the opening 208 or inlet to the microchannel 218 and a negative pressure is applied to the other opening 208 or inlet in order to drive solder 222 through the microchannel(s) 218. After the microchannel(s) 218 are filled with the liquid solder 222, the mold 216 is cooled to the room temperature. The resulting structure can be cut into a desired shape using a $CO_2$ laser.

The above described method of IOP sensing device 130 fabrication of the present technology employs solder-filled microchannels to form thick metal structures rather than electroplating. As a result, the present technology avoids use of the toxic solutions used in electroplating. Furthermore, the use of solder-filled microchannels allows the metal structures to be embedded in the encapsulant so that the metal electrode layer needed for electroplating is no longer necessary. This is expected to reduce material costs and increase throughput. Alloys are chosen based on indium content (e.g., to increase the wettability of the treated PDMS surface) and the melting point (e.g., to prevent exposing chips to high temperatures). For example, 51% In 32.5% Bi 16.5% Sn low-temperature solder (Indium Corp.) is often used for its melting point of 60° C. Other commercially available solders with relatively low melting points are described in the table in FIG. 14. Such solder materials, however, contain Hg or Pb and thus are classified as toxic and not a viable option for implantable devices.

Figure 16:
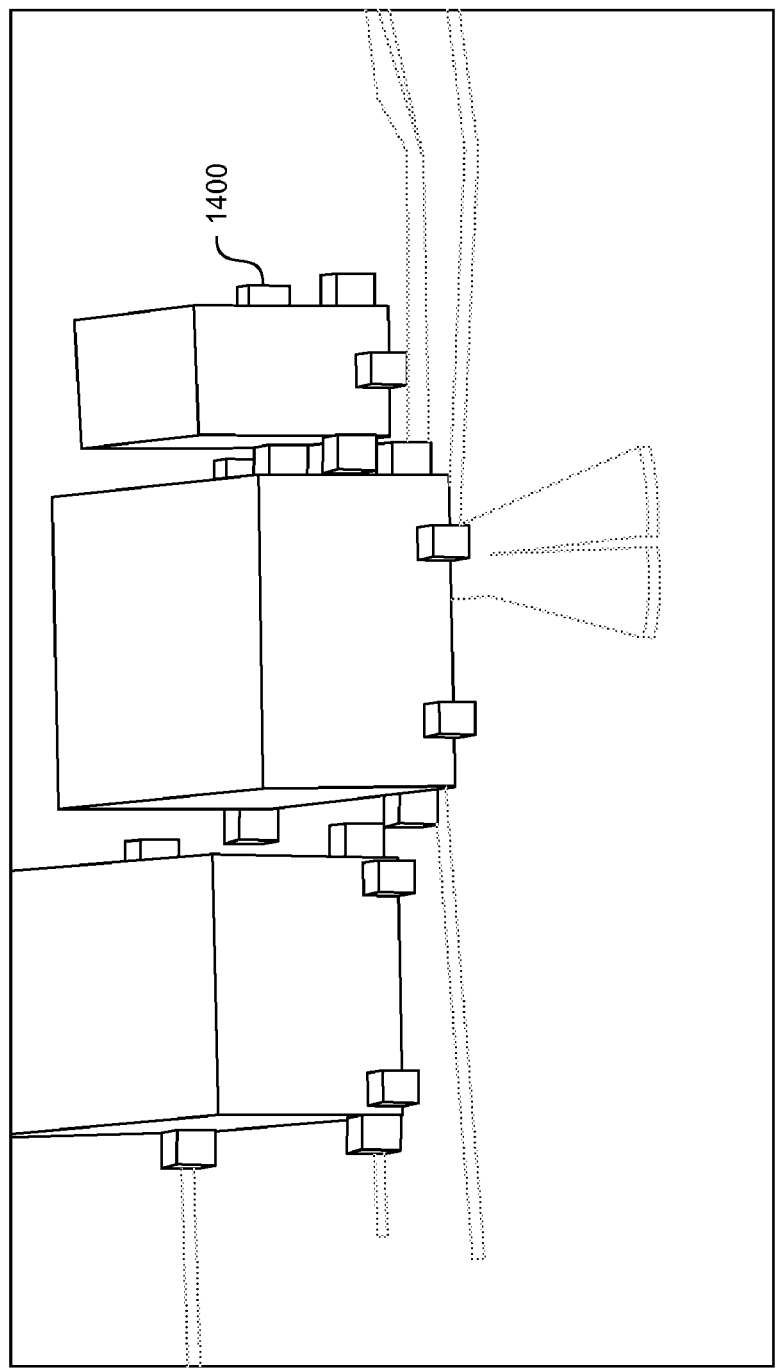
FIG. 16 shows an immobilizing structure configured in accordance with the present technology.

FIGS. 15A-15G illustrate another method for fabricating an IOP sensing device in accordance with embodiments of the present technology. The intermediate structures of FIGS. 15A, 15B and 15E are generally similar to those described in FIGS. 13B and 13C. FIG. 15C is a front view of an intermediate structure 303 including a microelectronic device 302 and a MEMS pressure sensor 305 immobilized on a substrate 304 (e.g., Si). The pressure sensor 305, microelectronic device 302 (collectively referred to as electronic structures 307) and/or other additional structures can be immobilized during fabrication, for example, by using magnets placed beneath the substrate 304. As shown in FIG. 16, in some embodiments, immobilizing structures 1400 (e.g., photoresist pillars) can be utilized to hold the electronic components in place.

As shown in FIG. 15C, a first polymer material 306 (e.g., a 10:1 PDMS mixture) can be formed on the substrate 304 and on and around the electronic structures 307. As shown in FIG. 15D, the first polymer material 306 can be detached from the intermediate structure 303, pulling the electronic structures 307 with it.

As shown in FIG. 15E, the first polymer material 306 can be inverted, and a surface 311 of the first polymer material 306 adjacent the exposed electronic structures 307 is then bonded to a surface 211 of the first polymer material 206 adjacent the ring-shaped indentation 210. The first polymer materials 206 and 306 are aligned for connecting the antenna pattern to the connection pads on the electronic structures 307. The resulting structure includes one or more microchannel(s) 318 where at least a portion of the floor of the microchannel includes an exposed contact pad for one or more electronic structures 307.

As shown in FIG. 15F, before solder delivery to the microchannel(s) 318, the microchannel(s) 318 can optionally be surface-treated 220 to enhance interaction between the newly formed polymer body 316 and the solder. Surface treatments, for example, can be similar to those described above with reference to FIG. 13F.

FIG. 15G is a front view of an intermediate structure 317 after solder delivery to the microchannel(s) 318. Before solder delivery, the dried polymer mold 316 can be heated to 75° C., above the melting point of the solder. A droplet of liquid solder is delivered to the opening 208 or inlet to the microchannel 318 and a negative pressure is applied to the other opening 208 or inlet in order to drive solder 322 through the microchannel(s) 318. After the microchannel(s) 318 are filled with the liquid solder 322, the mold 316 is cooled to room temperature. The resulting structure can be cut into a desired shape using a $CO_2$ laser or another suitable device.

It will be appreciated that any of the foregoing fabrication steps described with reference to FIGS. 15A-15B may include additional/different steps or processes.

IV. Selected Methods for Implanting an Intraocular Assembly

FIGS. 17A-17F illustrate a method for implanting an intraocular assembly 102 in accordance with an embodiment of the present technology. Although the method described herein is generally similar to cataract surgery methodology, any suitable implantation method may be used. Cataract surgery methodology can be an attractive procedural option because of the modern "microincision" trend in cataract surgeries. Also, both cataract and glaucoma are observed more often in an older population, after the age of 40. As a result, an IOP sensing device implanted during cataract surgery is expected to help early diagnosis of glaucoma in this part of the population.

Figure 17A:
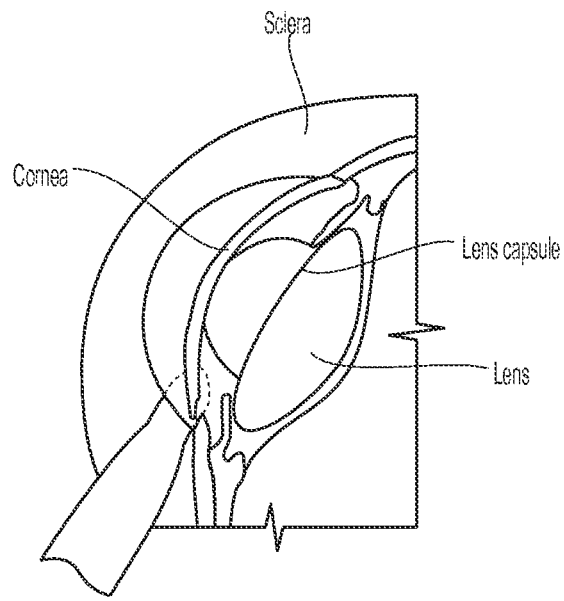
FIGS. 17A-17F illustrate a method for implanting an intraocular assembly in accordance with embodiments of the present technology.
Figure 17B:
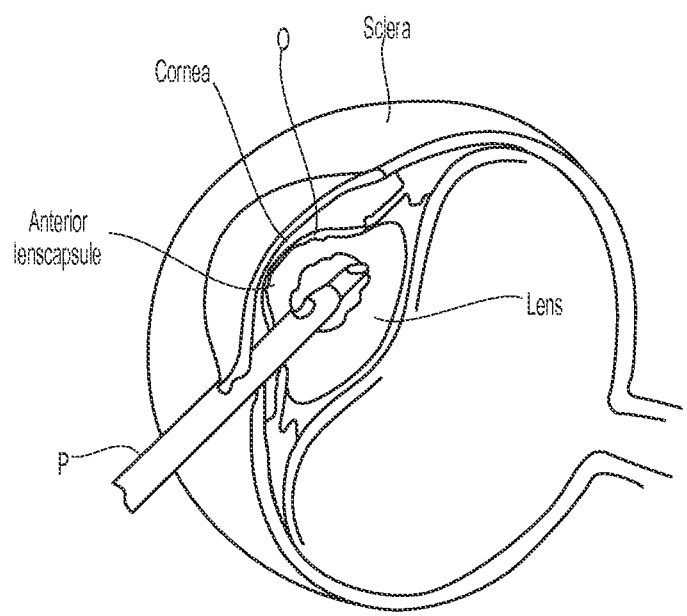
Figure 17C:
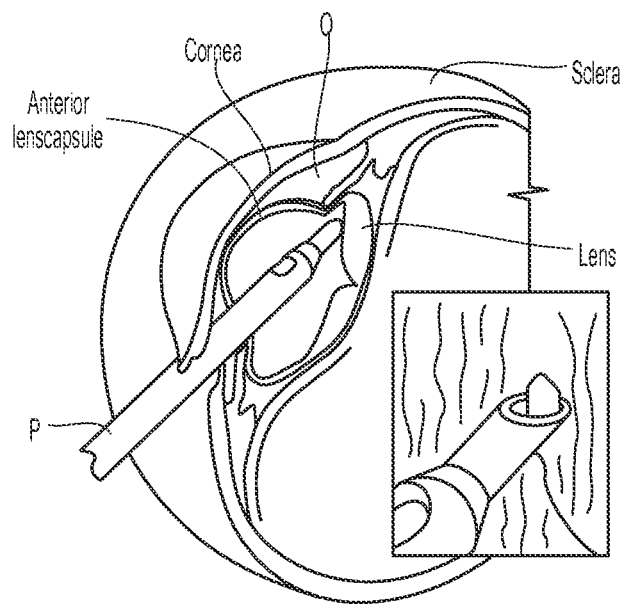
Figure 17D:
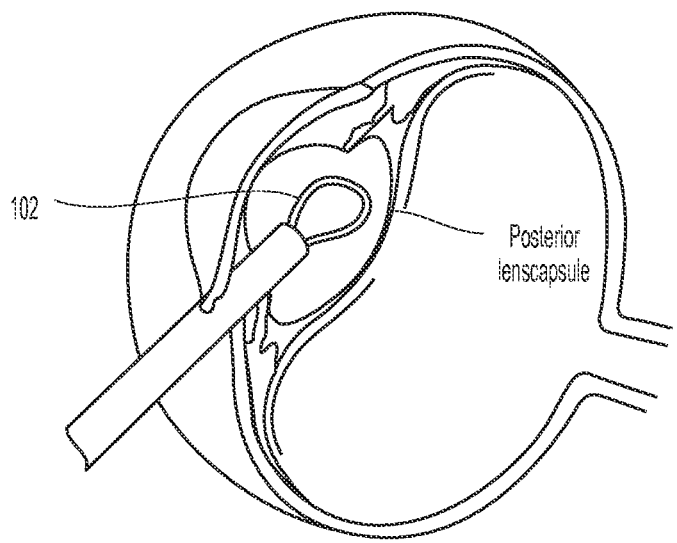
Figure 17E:
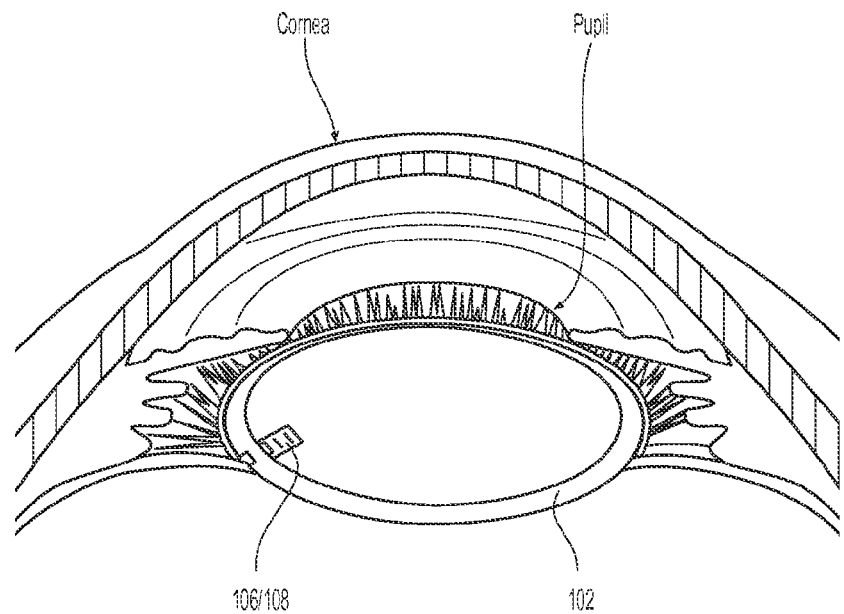
Figure 17F:
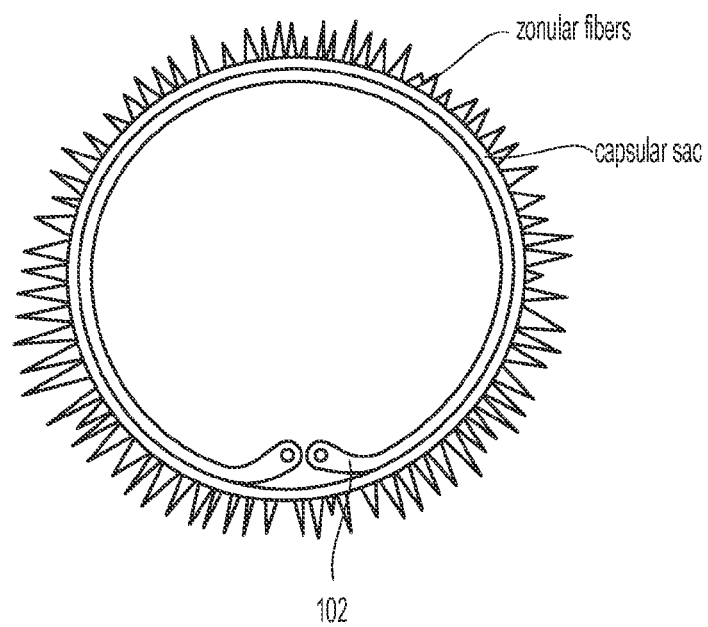

As shown in FIG. 17A, an incision (e.g., between about 1 mm to about 3 mm) is made in the eye where the cornea meets the sclera. During procedures that include complete or partial removal of the lens, a small, circular opening O is made in the anterior portion of the capsular bag and a phacoemulsification probe P is inserted into the eye (FIG. 17B). The probe P emits ultrasound energy to break the cataract into small pieces. As shown in FIG. 17C, the clinician then uses suction to remove the cataract and lens pieces from the eye. As shown in FIG. 17D, the intraocular assembly 102 is delivered to the capsular bag by an introducer in a folded or compressed configuration and allowed to expand inside the capsular bag. The fluid-induced shape memory material of the annular member 132 allows the assembly 102 to expand within the capsular bag and exert an outward force on the capsular bag and/or zonular fibers, thereby stabilizing the assembly 102 within the eye (FIG. 17E). In certain procedures, as illustrated by FIG. 17F, an IOL may subsequently be implanted and may utilize the assembly 102 as an additional support structure. For example, the IOL may have one or more supporting members 190 push radially outwardly against at least a portion of the circumference of the assembly 102 to secure the IOL within the capsular bag.

Conventional pressure sensing devices implanted in the anterior chamber make it difficult to align to charging device and the implanted device. Embodiments of the assembly 102 configured in accordance with the present technology, however, are embedded in a capsular tension ring that does not exhibit this problem since the ring is designed as an unmoving implant.

V. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An intraocular pressure ("IOP") monitoring system, the IOP system comprising:

an implantable intraocular assembly configured to be positioned within a capsular bag of a human eye, the assembly including
an annular member;
an IOP sensing device embedded within the annular member, the IOP sensing device comprising a microelectronic device having memory and processing circuitry, a pressure sensor configured to measure an intraocular pressure, and a first antenna configured to receive a radiofrequency ("RF") signal,
wherein the memory and processing circuitry are configured to convert a pressure measurement from the pressure sensor into a frequency measurement; and
an external unit configured to be positioned external of the patient, the external unit including
a second antenna configured to transmit an RF signal to the first antenna to charge the TOP sensing device,
wherein the microelectronic device is configured to passively transmit pressure sensing data to the external unit via RF backscatter.

2. The IOP monitoring system of claim 1 wherein the implantable intraocular assembly further includes an encapsulant that encapsulates at least a portion of the IOP sensing device.

3. The IOP monitoring system of claim 2 wherein the annular member is made of poly (ether urethane) ("PEU").

4. The IOP monitoring system of claim 2, wherein the encapsulant is made of polydimethylsiloxane ("PDMS").

5. The IOP monitoring system of claim 2, further including a temperature sensor in electrical connection with the microelectronic device and completely encapsulated by the encapsulant.

6. The IOP monitoring system of claim 2 wherein the encapsulant is torus-shaped.

7. The IOP monitoring system of claim 1 wherein the annular member has a torus shape and is made of a fluid-induced shape memory material.

8. An intraocular pressure sensing device configured to be implanted within an eye of a human patient, the intraocular pressure sensing device comprising:
a pressure sensor configured to measure an intraocular pressure of the eye of the patient via a capacitance measurement;
a microelectronic device in electrical connection with the pressure sensor, wherein the microelectronic device is configured to convert the capacitance measurement to a frequency signal; and
a single-turn loop antenna configured to receive RF electromagnetic energy to power the microelectronic device, wherein
the pressure sensor, the microelectronic device, and the antenna are completely encapsulated by an elastomeric encapsulant,
the microelectronic device is configured to passively transmit pressure sensing data to an external unit via RF backscatter, and
wherein the encapsulant is made of poly (ether urethane) ("PEU") and is radially expandable upon exposure to a fluid.

9. The intraocular pressure sensing device of claim 8 wherein the encapsulant is made of polydimethylsiloxane ("PDMS").

10. An intraocular pressure sensing device configured to be implanted within an eye of a human patient, the intraocular pressure sensing device comprising:
a pressure sensor configured to measure an intraocular pressure of the eye of the patient via a capacitance measurement;
a microelectronic device in electrical connection with the pressure sensor, wherein the microelectronic device is configured to convert the capacitance measurement to a frequency signal; and
a single-turn loop antenna configured to receive RF electromagnetic energy to power the microelectronic device, wherein
the pressure sensor, the microelectronic device, and the antenna are completely encapsulated by an elastomeric encapsulant,
the microelectronic device is configured to passively transmit pressure sensing data to an external unit via RF backscatter, and
the device has a compressed configuration and an expanded configuration, and wherein
in the compressed configuration, the device has a cross-sectional area of less than 2 $mm^2$, and
in the expanded configuration, the device has an outer diameter between about 10 mm and about 15 mm.

11. A method for manufacturing an intraocular pressure sensing device, the method comprising:
forming a ring-shaped photoresist structure on a substrate;
forming a first polymer structure on and around the photoresist structure on the substrate, wherein the first polymer structure includes a first surface facing the substrate and a second surface opposite the first surface and facing away from the substrate;
forming an opening in the first polymer structure that extends to the photoresist structure and is aligned with at least a portion of the photoresist structure;
removing the first polymer structure from the substrate;
bonding the second surface of the first polymer structure to a second polymer structure to create a microchannel, wherein the second polymer defines a bottom surface of the microchannel; and
filling at least a portion of the microchannel with a solder material, wherein the solder material is deposited in the microchannel through the opening in the first polymer structure.

12. The method of claim 11 wherein the first polymer structure and the second polymer structure together define a first encapsulant, and wherein the method further comprises surrounding the first encapsulant with a second encapsulant.

13. The method of claim 11 wherein the second polymer structure includes an electronic structure, and wherein filling at least a portion of the microchannel further comprises depositing the solder material on at least a portion of the electronic structure.

14. The method of claim 11, further comprising surface treating a portion of the second polymer structure within the microchannel.

15. The method of claim 11 wherein the first polymer structure and the second polymer structure together define an encapsulant, and wherein the method further comprises fabricating the encapsulant into a circular shape.

16. A method for implanting an intraocular assembly in an eye of a human patient, the method comprising:
forming an incision between 1 mm and 3 mm in length in the eye of the patient;
delivering the intraocular assembly in a compressed state to a capsular bag of the eye, wherein the intraocular assembly comprises
an annular member; and an IOP sensing device embedded within the annular member, the IOP sensing device comprising a microelectronic device, a pressure sensor configured to measure an intraocular pressure, and an antenna configured to receive a radiofrequency ("RF") signal, wherein the microelectronic device is configured to passively transmit pressure sensing data to an external unit configured to be positioned external of the patient via RF backscatter; and expanding the intraocular assembly at the capsular bag of the eye of the patient, wherein expanding the intraocular assembly includes exposing the annular member to a fluid within the eye.

17. The method of claim 16 wherein expanding the intraocular assembly includes asymmetrically expanding the assembly.

18. An intraocular pressure sensing device configured to be implanted within an eye of a human patient, the intraocular pressure sensing device comprising:

a pressure sensor configured to measure an intraocular pressure of the eye of the patient via a capacitance measurement;

a microelectronic device in electrical connection with the pressure sensor, wherein the microelectronic device is configured to convert the capacitance measurement to a frequency signal; and a single-turn loop antenna configured to receive RF electromagnetic energy to power the microelectronic device, wherein the pressure sensor, the microelectronic device, and the antenna are completely encapsulated by an elastomeric encapsulant, wherein the intraocular pressure sensing device is transformable between a compressed configuration and an expanded configuration, and wherein in the compressed configuration, the intraocular pressure sensing device has a cross-sectional area of less than 2 mm$^2$, and in the expanded configuration, the intraocular pressure sensing device has an outer diameter between about 10 mm and about 15 mm.

* * * * *